United States Patent [19]
Eubanks, Jr. et al.

[11] Patent Number: 5,899,919
[45] Date of Patent: * May 4, 1999

[54] MINIATURE ENDOSCOPIC SURGICAL INSTRUMENT ASSEMBLY AND METHOD OF USE

[75] Inventors: William S. Eubanks, Jr.; William L. Athas, both of Durham; Marvin E. York; Leon R. Substelny, both of Raleigh, all of N.C.

[73] Assignee: Mist, Inc., Smithfield, N.C.

[ * ] Notice: This patent is subject to a terminal disclaimer.

[21] Appl. No.: 08/943,466

[22] Filed: Oct. 3, 1997

Related U.S. Application Data

[60] Continuation of application No. 08/654,111, May 28, 1996, abandoned, which is a division of application No. 08/390,625, Feb. 17, 1995, Pat. No. 5,593,420.

[51] Int. Cl.⁶ .................................................. A61B 17/00
[52] U.S. Cl. ......................... 606/205; 606/170; 606/174
[58] Field of Search ................................ 606/1, 108, 170, 606/171, 180, 174, 205–211; 600/564–567

[56] References Cited

U.S. PATENT DOCUMENTS 5,312,391   5/1994   Wilk ........................................ 606/205

*Primary Examiner*—Gary Jackson
*Assistant Examiner*—William Lewis
*Attorney, Agent, or Firm*—Jenkins & Wilson, P.A.

[57] ABSTRACT

An endoscopic surgical instrument assembly including a support sheath, a miniature medical implement member, and a securing mechanism for securing the support sheath and the medical implement member together in fixed relationship. The securing mechanism is adapted for securing the miniature medical implement member and the support sheath to one another when the miniature medical implement member is advanced axially through the support sheath so that the implement member and the support sheath form a co-axial unit. As a result, the support sheath provides rigid support for the miniature medical implement member and prevents the elongated portion thereof from breaking during an endoscopic medical procedure.

17 Claims, 9 Drawing Sheets

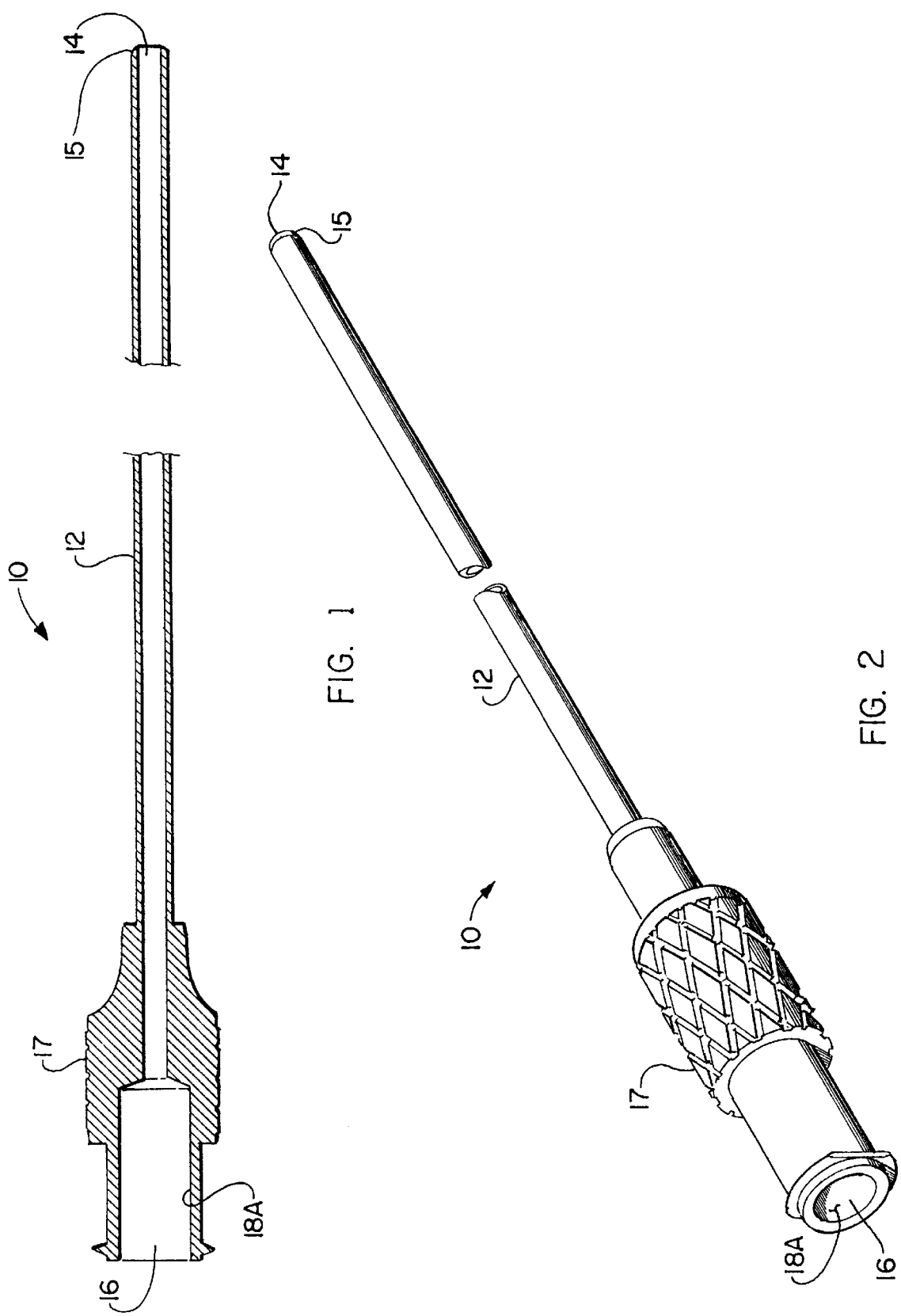

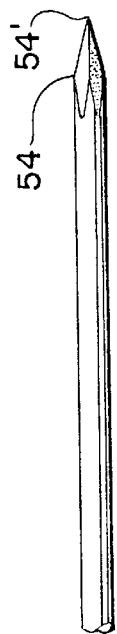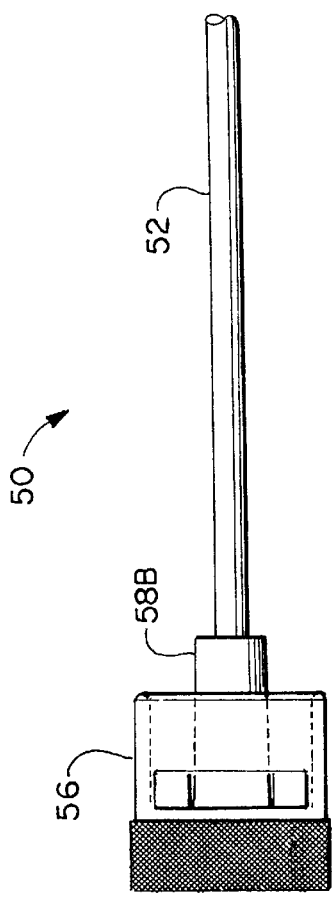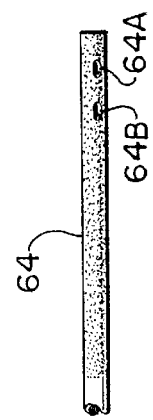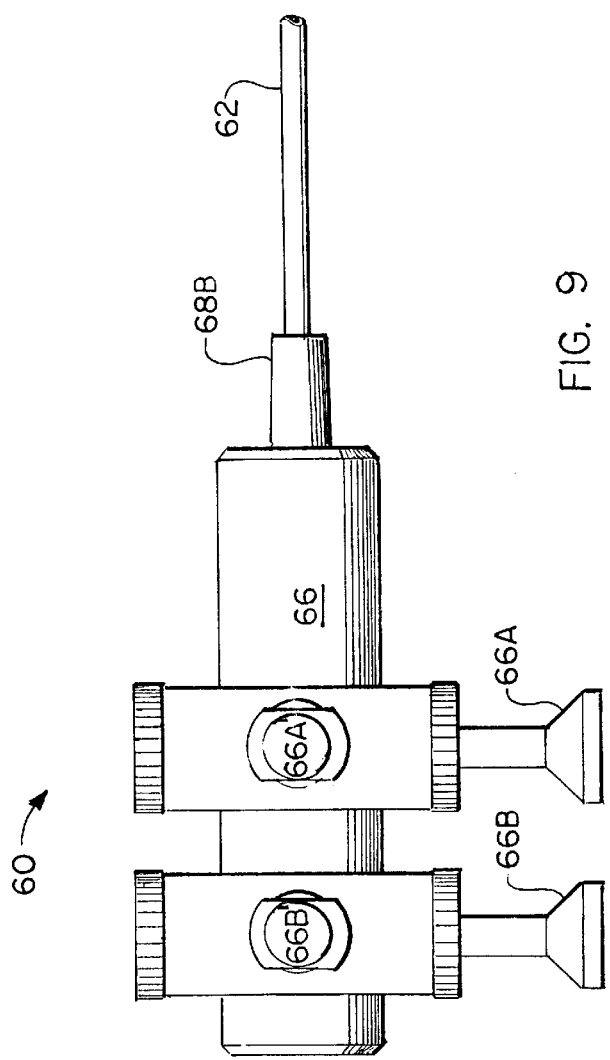
FIG. 8
FIG. 9

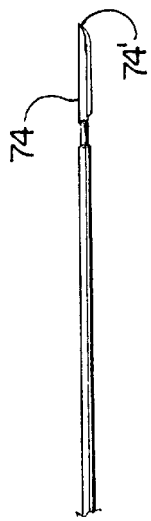
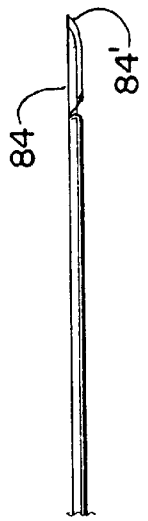
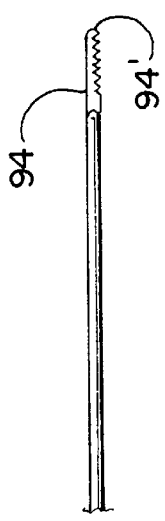
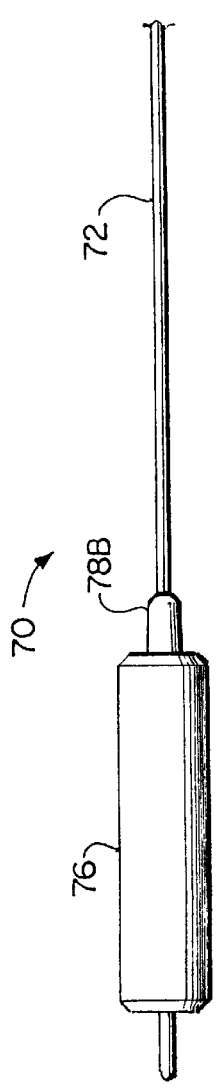
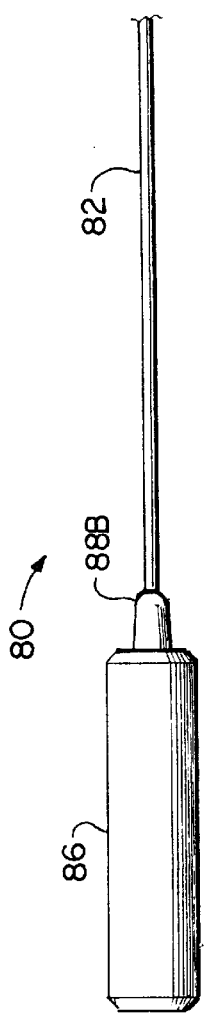
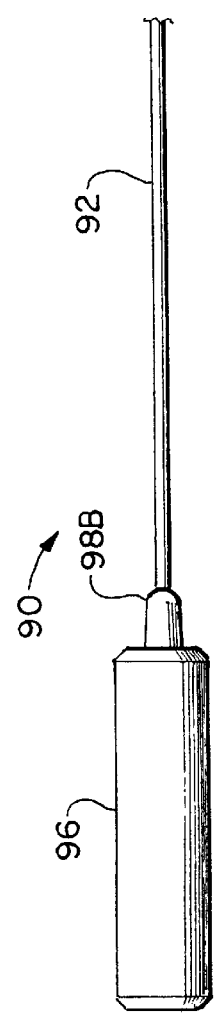
FIG. 10
FIG. 11
FIG. 12

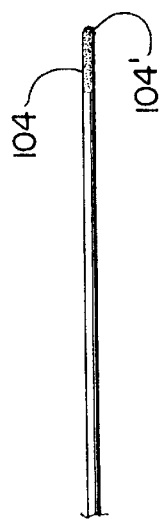
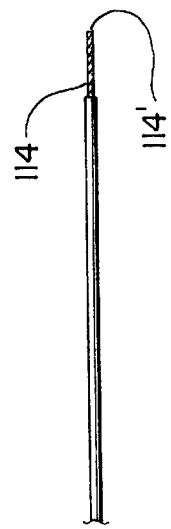
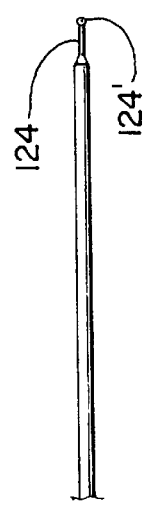
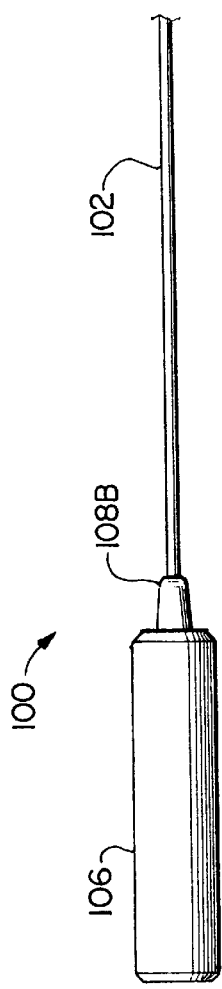
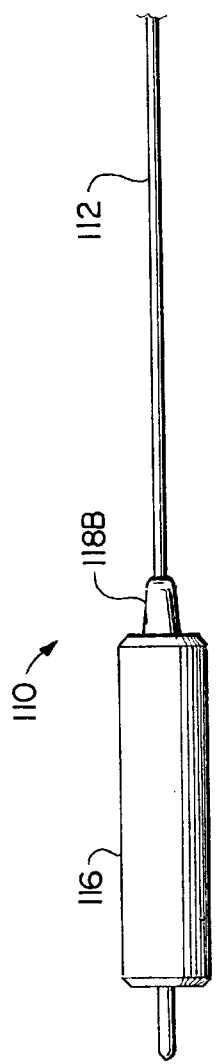
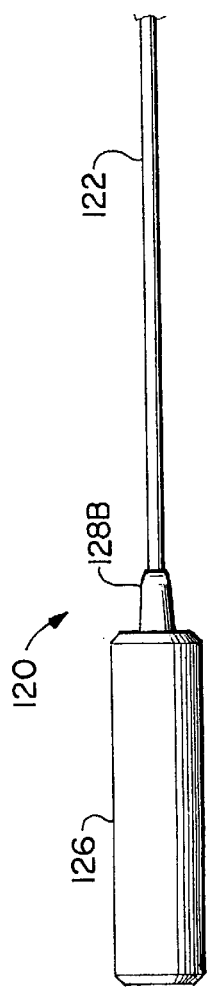
FIG. 13
FIG. 14
FIG. 15

MINIATURE ENDOSCOPIC SURGICAL INSTRUMENT ASSEMBLY AND METHOD OF USE

RELATED APPLICATION

This is a continuation of application Ser. No. 08/654,111 filed on May 28, 1996, now abandoned which is a divisional application of U.S. patent application Ser. No. 08/390,625 filed on Feb. 17, 1995, and now U.S. Pat. No. 5,593,420.

TECHNICAL FIELD

The present invention relates generally to endoscopic medical implements, and more particularly to a surgical instrument assembly that is a combination sheath and miniature endoscopic medical implement such that the sheath provides rigid support to the implement during an endoscopic medical procedure and thereby prevents the miniature implement from bending or breaking during the procedure.

BACKGROUND OF THE INVENTION

Endoscopic procedures gain access to the inside of a human or veterinary body by using a cutting instrument to pierce or puncture bodily tissues (i.e., skin, muscles, membranes, or the like), and then a narrow cannula is inserted through the puncture wound as a guideway for access to the body interior. The cannula is narrow as the area in which the surgeon must perform procedures incorporating endoscopic medical instrumentation is smaller than that normally encountered when conventional surgical techniques are employed. As a result, endoscopic medical procedures are minimally invasive and leave minimal scarring for the patient.

More particularly, in endoscopic procedures, various implements are inserted through the skin and body wall into the body, wherein surgical procedures are to be undertaken. The interior operating site is "visualized" by employing an endoscope or viewing port that also extends into the body. While the surgeon may view the interior of the body directly through the endoscope, usually, the endoscope is connected to a camera and television monitor that presents a magnified view of the body interior for the surgeon to view. By viewing the interior, the surgeon can conduct operative procedures by employing different narrow implements.

To allow for better visualization of the body interior and easier access to the operative site, an insufflation procedure may possibly be employed depending on the specific operative site. During insufflation, a gas, typically carbon dioxide, is injected into the body to initiate enlargement of the area where surgery is to be performed and maintain that area in enlarged form. To achieve insufflation, a first puncture or stab wound is made and then a narrow pneumoperitoneum insufflation needle (called a Veress-type needle) is used to puncture the body wall and the gas is introduced through the needle. Insufflation is especially used when the surgical area is the abdominal cavity, and the endoscopic procedure is a laparoscopic procedure. However, it is to be kept in mind that endoscopic procedures are increasingly being employed for surgery in various other body areas, such as for arthroscopic surgery on joints or for insertion of breast implants. One method of placing these implants is by way of the bikini line below the patient's waist so that any scars from the breast enlargement surgery are at the bikini line instead of at the breast area.

After a pneumoperitoneum is adequately established (or in the event of surgery such as on a knuckle joint where there is no pneumoperitoneum) and the endoscope is in place, additional puncture or stab wounds may be made for the narrow endoscopic implements. A tubular sheath (commonly called a cannula) is inserted through the puncture wound while a cutting instrument (commonly called a trocar) is disposed inside of the sheath with the cutting edge of the trocar protruding past the end of the sheath. The cannula and trocar are gently advanced into the body under direct visualization. The sharp cutting tip of the trocar cuts the way for the cannula to be advanced into the body, and sometimes only a cannula (without any trocar) having a sharp cutting tip for advancement into the body is used.

The sheath is left in place (advanced through the puncture wound in the body) in order to gain access within the body. Thus, the sheath keeps the puncture wound open, and then the trocar (if one has been used) is removed so that now the sheath provides an access channel or guideway for narrow endoscopic implements other than a trocar to be inserted through the tubular hole of the sheath so that surgery can be performed inside the body.

For instance, forceps (commonly called graspers) may be placed through the sheath so that the bowel may be grasped, the liver retracted, or the peritoneal surface grasped with the working end of the forceps. Next, the forceps may be removed from the sheath and a cautery placed therethrough so that micro-hemostasis can be achieved using electrocautery.

As noted hereinabove, endoscopic medical implements are small so that instrumentation is smaller than that encountered with conventional surgical techniques. As a result, endoscopic procedures result in significantly less trauma than that from conventional invasive surgery and also lead to typically much shorter recovery time for the patient. Of course, the smaller the endoscopic implements are, then the less invasive the endoscopic procedure is.

For current commercial implements, the elongated, cylindrical portion of an endoscopic medical implement is typically about 5 mm to about 10 mm in cross-sectional diameter, and the tubular cannula to provide guidance therefore typically has an internal diameter of about 11 mm in cross-section. Such endoscopic medical implements are made of plastic or metal, and a limiting factor in the smallness of the diameter has been found because if they are manufactured too thin and narrow, they would be fragile and would easily snap or break inside of the body, leaving the working end of the implement inside of the body. Then, conventional invasive surgery with a large cut area would have to be performed in order to remove from the body the working end that had broken off of the endoscopic medical implement.

To date, no satisfactory way has been found to employ extremely small diameter endoscopic implements and thus make endoscopic procedures even less invasive than they currently are without having the danger of the working end of the implement breaking off inside of the body. Nevertheless, the following patents are of general background interest vis-a-vis endoscopic implements and/or sheaths (cannulas) for insertion of implements therethrough and into the body either through a puncture wound or a body orifice.

U.S. Pat. No. 5,355,871 to Hurley et al., assignors to Dexide, Inc., involves a cylindrical housing as a guideway for an endoscopic surgical instrument. The instrument is concentrically disposed interior of the housing and movable between first and second positions. The housing includes a flexible, dome-like portion that is located for engagement by the thumb and forefinger of a human operator and overlies a portion of the endoscopic surgical instrument. As the flexible portion is grasped and compressed with the thumb and forefinger, the endoscopic surgical instrument is held in place inside of the cylindrical housing. A drawback is that if the human operator should inadvertently loosen the grip of the thumb and forefinger, the endoscopic surgical instrument will slide and move to a different position inside of the cylindrical housing.

U.S. Pat. No. 5,364,365 to Wortrich, assignor to Surgin Surgical Instrumentation, Inc., discloses an elongated surgical instrument for penetrating into a body cavity. The instrument has an obturator with a cutting cannula. The obturator is spring-mounted so that it will retract within the cannula when the cannula encounters a body wall, but also so that it will move to an extended distal position inside the body cavity. The obturator can be locked in an axial position when it is in the extended distal position so that the instrument can be used in a surgical procedure without danger of cutting internal tissue or organs. Thus, the obturator is a safety device that facilitates use of instruments during laparoscopic surgery.

Various needle assemblies that include an introducer needle having another member movable therein between different positions are shown in U.S. Pat. No. 5,312,375 to Gurmarnik (no assignee); U.S. Pat. No. 5,292,310 to Yoon (no assignee); and U.S. Pat. No. 5,057,085 to Kopans, assignor to Medical Device Technologies, Inc. In the patent to Gurmarnik, the other member is a spinal needle. In the patent to Yoon, the other member is a safety probe. In the patent to Kopans, the other member is a trocar. Each of the devices in these three patents is provided with a set screw for locking in place the member that moves from a first position to a second position within the introducing needle.

Also, of some relevance vis-a-vis an assembly with an outer sheath and a removable instrument located therewithin is U.S. Pat. No. 4,461,280 to Baumgartner (no assignee). This patent involves a method for medical treatment of the prostate area with a urethrally inserted apparatus assembly. The apparatus assembly has an outer sheath and a removable obturator located within the sheath during insertion of the assembly into the urinary tract by way of the urethral orifice in the penis. One end of the sheath is configured to retain the tip of the obturator, and the other end of the sheath is rigidly retained in a mounting member and extends through the mounting member and a locking member of conventional construction. The mounting member retains the locking member so that it will rotate relative to the mounting member in order to align slots for receiving the obturator. When the obturator is inserted into the sheath, projecting pins engage those slots and the locking member can be rotated to retain the obturator securely in position. Once the sheath is in position in the selected area, the obturator is removed from the sheath and a sampling implement having a harpoon-blade working end is inserted into and through the sheath to a location adjacent the selected area of the prostate. The harpoon end has both a tip (which is used to puncture the tissue to be sampled) and a pocket behind the tip (which is used for collecting the tissue sample).

Finally, U.S. Pat. No. 5,312,391 to Wilk (no assignee) discloses a laparascopic instrument assembly comprising a rigid sleeve and a multiplicity of laparascopic instrument shafts inserted inside the sleeve. The instrument assembly is intended to be inserted through a laparascopic cannula during surgery to provide an increased number of available instruments without increasing the number of abdominal perforations in a patient. However, the instrument assembly does not provide for affixing a surgical instrument to the sleeve for enhanced performance as a new unitary mechanism, but merely provides a locking mechanism to remove the working end of selected instruments from the surgical field when another instrument is being used.

OBJECTS AND SUMMARY OF THE INVENTION

In accordance with the present invention, a miniature surgical instrument assembly is provided for performing an endoscopic medical procedure in a human or veterinary body. The assembly comprises a support sheath, a miniature medical implement member, and a securing mechanism for immovably fixing said medical implement member and said support sheath with one another.

More particularly, the support sheath has an elongated tubular portion, a distal end, and a proximal end. The support sheath is adapted for introduction into a tissue forming part of the body and for advancement therewithin. The miniature medical implement member has an elongated portion, a working end, and a handle end. The medical implement member is adapted for insertion into and advancement axially through the support sheath until the working end extends beyond the distal end of the support sheath. The securing mechanism is adapted for immovably fixing the miniature medical implement member and the support sheath with one another at their handle end and proximal end, respectively, when the miniature medical implement member is advanced axially through the support sheath with the working end extending beyond the distal end of the support sheath to form a co-axial unit. As a result, when the miniature medical implement member is immovably fixed to the support sheath, the support sheath provides rigid support and will during the endoscopic medical procedure in the body prevent the elongated portion of the miniature medical implement member from breaking.

Also, the present invention provides a medical process for performing an endoscopic medical procedure in a target area within a human or veterinary body. The medical process comprises first providing a support sheath having an elongated tubular portion, a distal end, and a proximal end, and advancing the sheath through a puncture wound in the body with the proximal end outside of the body and the distal end inside of the body. As a result, access within the body is gained and the support sheath is in position in the target area.

Next, the process involves inserting into the support sheath a miniature medical implement member having an elongated portion, a working end, and a handle end. As the miniature medical implement member is being inserted, it is advanced axially through the support sheath until the working end extends beyond the distal end of the support sheath.

Thereafter, the process involves immovably fixing, via a securing mechanism, the miniature medical implement member and the support sheath with one another at their handle end and proximal end, respectively, when the miniature medical implement member is advanced axially through the support sheath with the working end extending beyond the distal end of the support sheath to form a coaxial unit. After forming the coaxial unit, the process then involves performing the endoscopic medical procedure using the unit within the body, whereby the support sheath provides rigid support for the miniature medical implement member. As a result, the miniature medical implement member is prevented from breaking during the endoscopic medical procedure.

Accordingly, it is an object of the present invention to provide a miniature surgical instrument assembly for use during endoscopic medical procedures so that miniature (i.e., extremely small diameter or thin) implements can be used during endoscopic surgery and the miniature implements do not bend or break during the surgery.

Thus, it is an advantage of the present invention that there is avoided having a broken-off working end of a miniature endoscopic medical implement lodged inside the body, whereby if so lodged, it would have to be removed with conventional surgical techniques causing greater trauma and longer recovery time for the patient.

Some of the objects of the invention having been stated hereinabove, other objects will become evident as the description proceeds, when taken in connection with the accompanying drawings as best described hereinbelow.

BRIEF DESCRIPTION OF THE DRAWINGS

FIG. 1 is a vertical cross-sectional view of the sheath portion of the present invention;

FIG. 2 is a perspective view of the sheath portion of FIG. 1;

FIG. 8 is a side elevational view of a representative miniature medical implement portion, illustrated as a trocar, of the present invention;

FIG. 9 is a side elevational view of a representative miniature medical implement portion, illustrated as an irrigation-aspiration probe with trumpet valves, of the present invention;

FIG. 10 is a side elevational view of a representative miniature medical implement portion, illustrated as a electro-surgical scalpel, of the present invention;

FIG. 11 is a side elevational view of a representative miniature medical implement portion, illustrated as a scalpel, of the present invention;

FIG. 12 is a representative miniature medical implement portion, illustrated as a scraper, of the present invention;

FIG. 13 is a side elevational view of a representative miniature medical implement portion, illustrated as a manipulator, of the present invention;

FIG. 14 is a side elevational view of a representative miniature medical implement portion, illustrated as a electro-surgical needle, of the present invention; and FIG. 15 is a side elevational view of a representative miniature medical implement portion, illustrated as a ball probe, of the present invention.

DETAILED DESCRIPTION OF A PREFERRED EMBODIMENT

Figure 3:
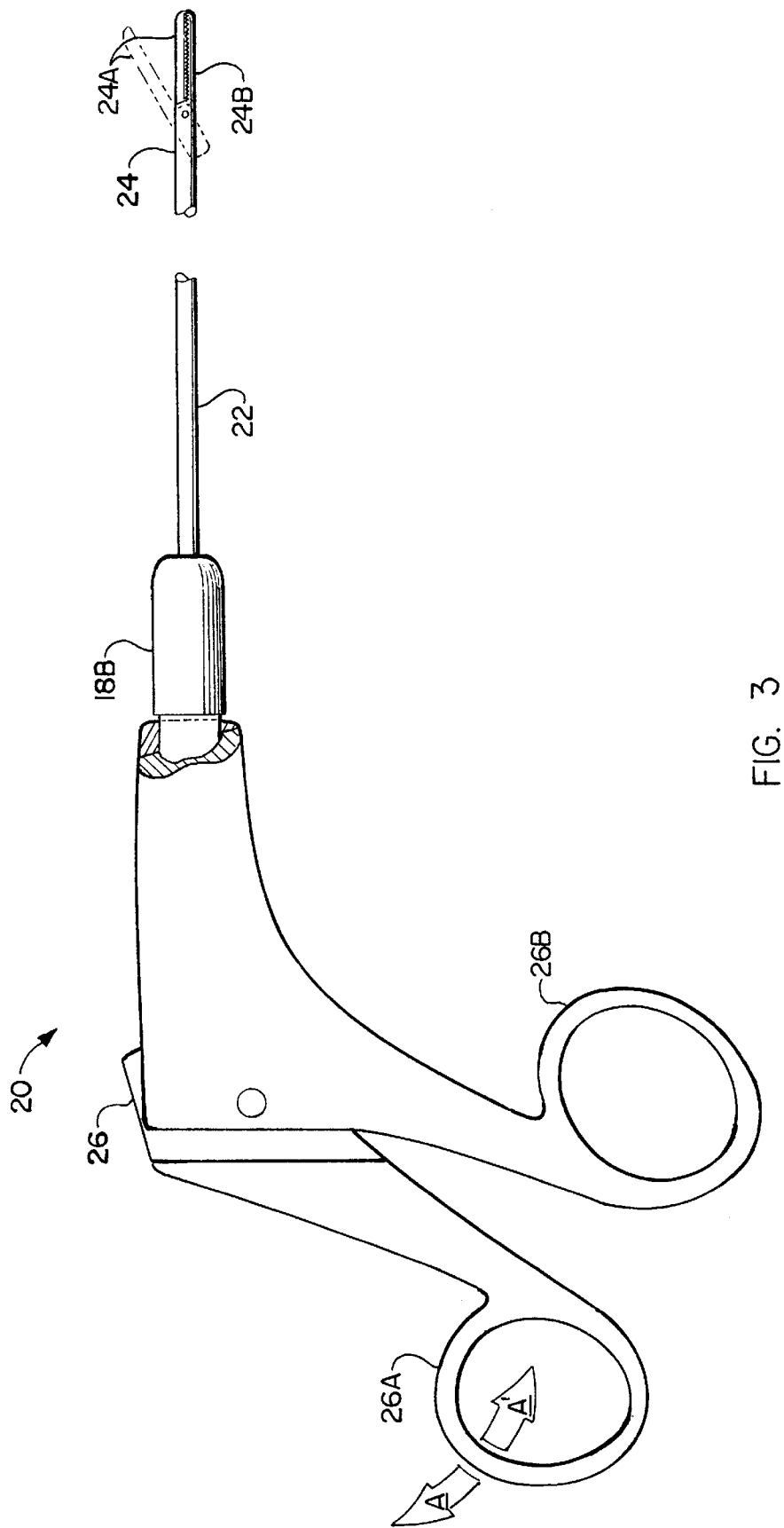
FIG. 3 is a side elevational view of a representative miniature medical implement portion, illustrated as a forceps (grasper), of the present invention.

Referring now to the drawings, FIGS. 1 and 2 show a vertical cross-sectional view and a perspective view, respectively, of miniature support sheath 10, which may most suitably be a cannula. Support sheath 10 has elongated, tubular portion 12 of generally hollow cylindrical shape, distal opening 14 located at distal end 15 thereof, and proximal opening 16 located at proximal end 17 thereof. Distal end 15 is shown as blunt and flat where it terminates, but it may also be made so that it terminates with an angled cutting edge (not illustrated). Also, located at proximal end 17 is female receiving portion 18A, which is a generally cup-shaped cavity of a securing mechanism 18 comprising female portion 18A and male portion 18B and which is described in detail hereinafter.

Referring now to FIG. 3, shown is representative miniature medical implement member 20, suitably illustrated as a forceps, commonly called a grasper. Miniature medical implement member 20 has elongated portion 22 of generally cylindrical shape, working end 24, and handle end 26. Additionally, illustrated at handle end 26 is male insertion portion 18B of securing mechanism 18 for making engagement with female receiving portion 18A (noted in the above discussion of FIGS. 1 and 2).

For the particular grasper 20 illustrated in FIG. 3, working end 24 is suitably a grasping mechanism having first grasping arm 24A and second grasping arm 24B. For ease of illustration, grasping arms 24A, 24B are shown in the closed position, with first grasping arm 24A again shown in broken lines to depict the open position. Grasping arms 24A, 24B are connected in a manner known to the person of ordinary skill in the art, such as by a rod wire (not illustrated), to handle end 26 in order to work grasping arms 24A, 24B so that they can grasp an organ such as the liver (not illustrated) to move it out of the way for surgery. More particularly, handle end 26 is suitably illustrated as a scissors handle, having first scissors handle arm 26A and second scissors handle arm 26B that move relative to each other as per arrows A, A' in a manner well known to those skilled in the art in order to work grasping arms 24A, 24B of grasper 20.

Figure 4:
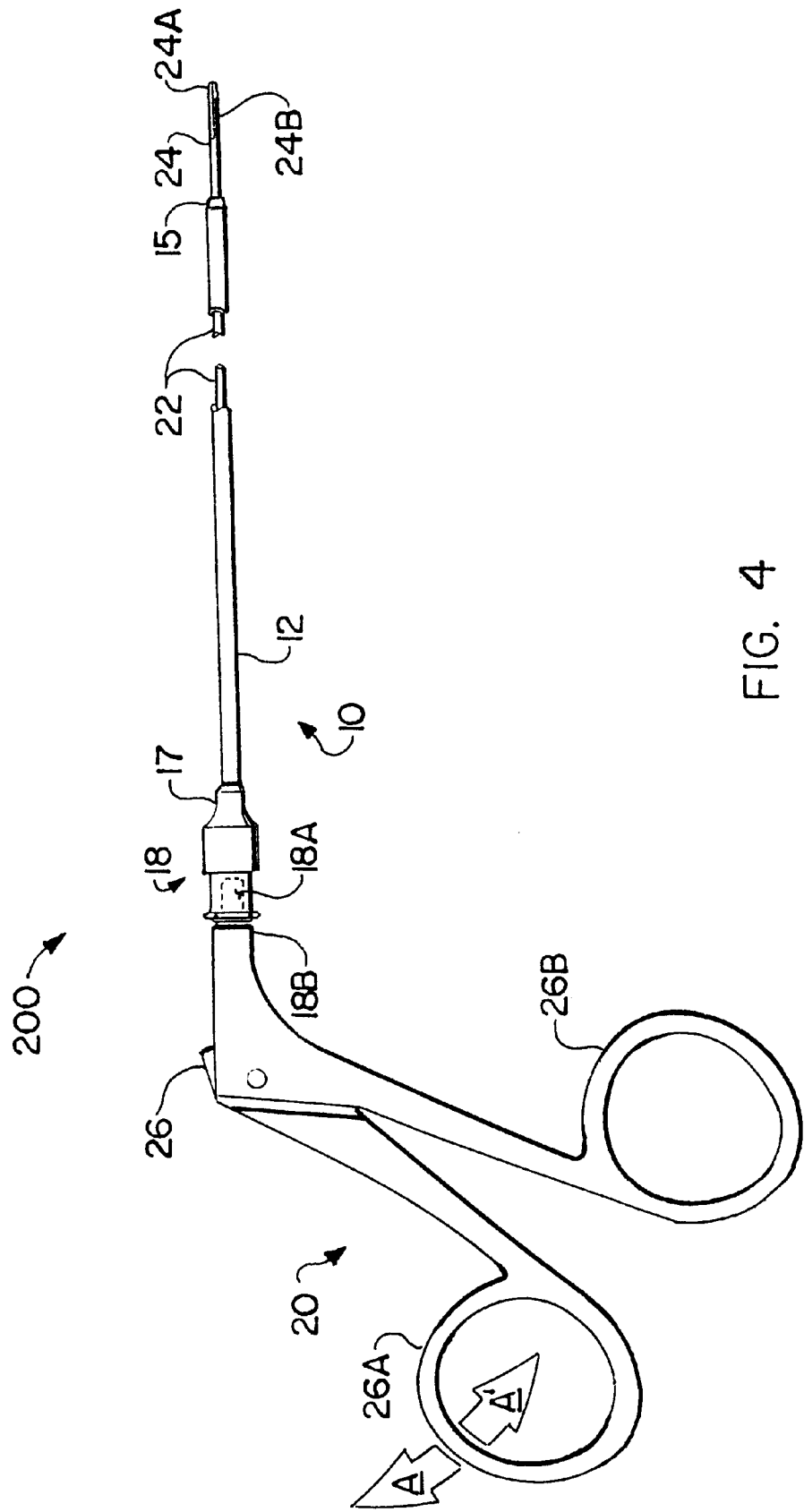
FIG. 4 is a side elevational view of a representative assembly of the sheath portion of FIG. 1 in combination with the representative miniature medical implement portion of FIG. 3 located therewithin, in accordance with the present invention.

Looking now at FIG. 4, surgical instrument assembly 200 is shown having representative miniature medical implement 20 removably coupled inside of sheath 10, and for ease of illustration, implement 20 is shown as the grasper that is illustrated in FIG. 3. Nevertheless, various other miniature medical instruments may be employed, which is discussed in more detail below vis-a-vis FIGS. 6–15.

As can be seen in FIG. 4, assembly 200 comprises support sheath 10, representative miniature medical implement member 20, and securing mechanism 18.

More particularly, support sheath 10 has elongated, tubular portion 12, distal end 15, and proximal end 17. Support sheath 10 is adapted for introduction into a tissue forming part of a human or veterinary body (not illustrated) and for advancement therewithin. Miniature medical implement 20 has elongated portion 22, working end 24, and handle end 26. Miniature medical implement member 20 is adapted for insertion into and advancement axially through support sheath 10, vis-a-vis opening 16 (see FIGS. 1 and 2), until working end 24 extends axially along elongated portion 12 through opening 14 (see FIGS. 1 and 2) and beyond distal end 15 of support sheath 10.

Securing mechanism 18 is adapted for securing miniature medical implement member 20 and support sheath 10 to one another at their handle end 26 and proximal end 17, respectively, when miniature medical implement member 20 is advanced axially through support sheath 10 with working end 24 extending beyond distal end 15 of support sheath 10, and thereby forming a co-axial unit. As a result, when miniature medical implement member 20 is secured to support sheath 10, support sheath 10 provides rigid support and will, during an endoscopic medical procedure in the body, prevent elongated portion 22 of miniature medical implement member 20 from breaking.

Therefore, it is contemplated that assembly 200 is useful in a medical process for performing endoscopic medical procedures. In use, the medical process for performing an endoscopic medical procedure in a target area within a human or veterinary body (not illustrated) first comprises providing miniature support sheath 10 having elongated, tubular portion 12, distal end 15, and proximal end 17, and advancing sheath 10 with a suitable trocar 50 fixedly secured therein so as to produce and/or pass through an existing puncture wound in the body (not illustrated), with proximal end 17 outside of the body and distal end 15 inside of the body. As a result, access within the body is gained and support sheath 10 is in position in the target area subsequent to removal of trocar 50.

Next, the process comprises inserting a representative miniature medical implement, such as grasper 20, having elongated portion 22, working end 24, and handle end 26, into sheath 10 by way of opening 16 therein. As miniature medical implement 20 is inserted, it is advanced axially through support sheath 10 until working end 24 comes out of opening 14 and extends beyond distal end 15 of support sheath 10.

Thereafter, the process comprises securing, via securing mechanism 18, miniature medical implement member 20 and support sheath 10 with one another at their handle end 26 and proximal end 17, respectively, when miniature medical implement member 20 is advanced axially through support sheath 10 with working end 24 extending beyond distal end 15 of support sheath 10 to form a co-axial unit. Lastly, the process involves performing the endoscopic medical procedure using the co-axial unit within the body, wherein support sheath 10 provides rigid support for miniature medical implement member 20 such that miniature medical implement member 20 is prevented from breaking along its elongated portion 22 during the endoscopic medical procedure.

It is preferred that elongated portion 12 of support sheath 10 have a cross-sectional outside diameter of about 0.083 inch (about 2.1 mm) to about 0.087 inch (about 2.2 mm) and a cross-sectional inside diameter of about 0.073 inch (about 1.85 mm) to about 0.077 inch (1.95 mm). Also, it is preferred that elongated portion 22 of miniature medical implement member 20 (and working end 24 so that miniature medical implement member 20 may be inserted into and axially advanced through sheath 10) have an outside diameter of about 0.068 inch (about 1.73 mm). Thus, left is a tolerance of about 0.005 inch (about 0.127 mm) to about 0.015 (about 0.254 mm) between the outside diameter of elongated portion 22 and the inside diameter of elongated portion 12. Of course, the cross-sectional outside diameter of elongated portion 22 may be smaller, even as small as about 0.068 inch (about 1.70 mm).

Such small diameters for portion 22 result, of course, in implement 20 being miniature and consequently fragile so that working end 24 could easily break off inside of the body during surgery, absent the rigid support provided by sheath 10 which is securely fixed to implement member 20 by way of securing mechanism 18 as will be described in more detail below in connection with FIG. 5.

For most endoscopic surgery, such as laparoscopic surgery through the patient's naval, miniature medical implement member typically has a length of about 22 cm to about 26 cm. Support sheath 10 is typically about 20.5 cm to about 24.5 cm in length, depending on the medical implement employed, so that the handle end and the working end of the implement can protrude out of the ends of the support sheath.

For orthopedic surgery, miniature medical implement member may be as small as about 5 cm to about 14 cm in length, and for breast implant surgery the miniature medical implement member may be as large as about 40 cm to about 50 cm in length. Hence, appropriate support sheaths may range from about 3.5 to about 48.5 cm in length. More particularly, for use with an orthopedic miniature medical implement member, a suitable length for the sheath is about 3.5 cm to about 12.5 cm, and for use with a breast implant miniature medical implement member, a suitable length for the sheath is about 38.5 cm to about 48.5 cm.

Figure 5:
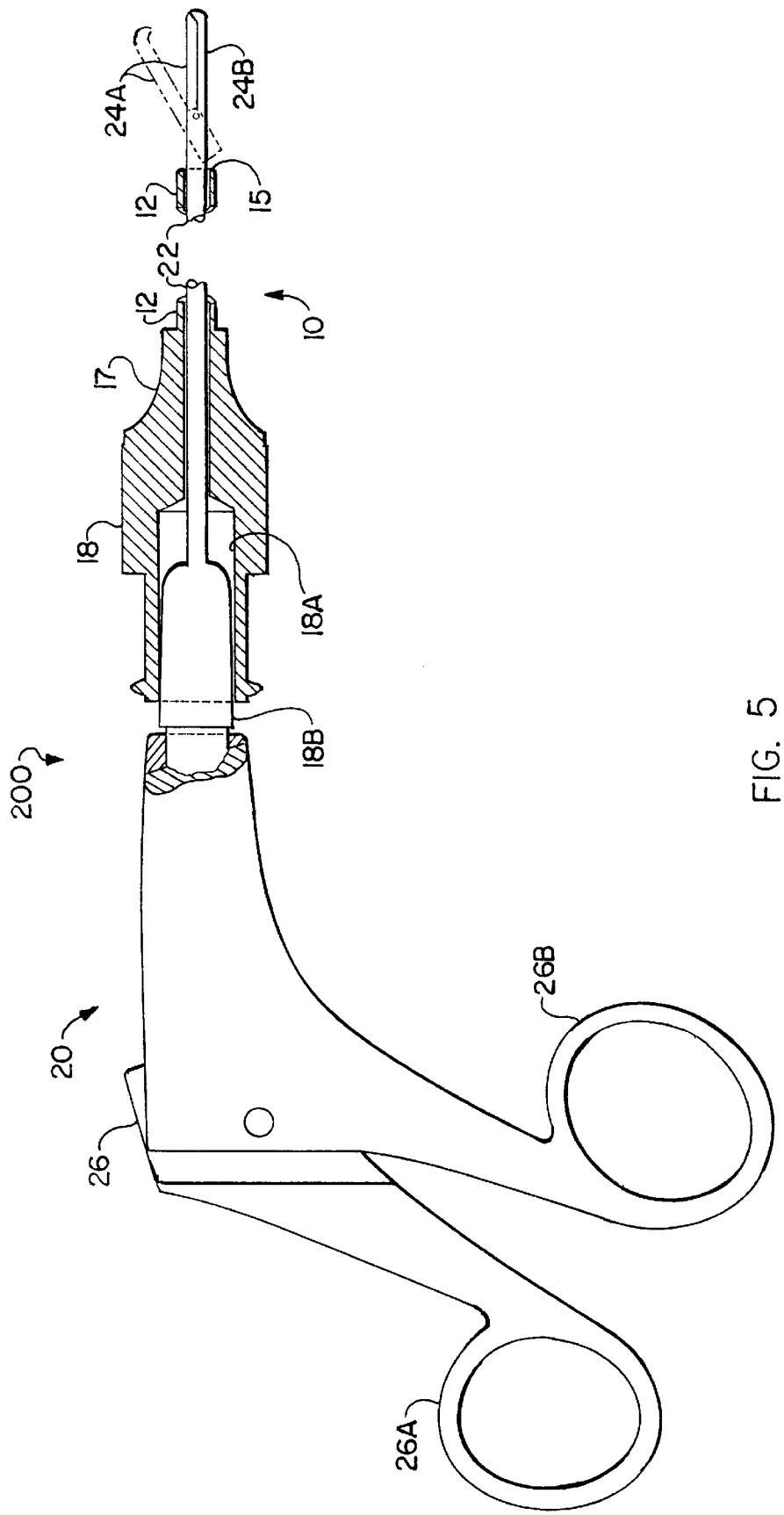
FIG. 5 is a vertical cross-sectional view of the assembly of FIG. 4, and in particular of the securing mechanism portion thereof.

With reference now to FIG. 5, illustrated therein is a vertical cross-sectional view of assembly 200 of FIG. 4, and in particular a vertical cross-sectional view of securing mechanism 18 can be clearly seen therein. Securing mechanism 18 comprises two components, namely female portion 18A and male portion 18B. As noted above, female portion 18A is located at proximal end 17 of sheath 10 and male portion 18B is located at handle end 26 of miniature medical implement member 20. Female portion 18A and male portion 18B provide for mating engagement with each other, which may suitably be a press fit as is best illustrated in FIG. 5.

However, other means of removably securing sheath 10 and miniature medical implement member 20, such as a twist-lock mechanism (not illustrated) or screw threads (not illustrated) on male portion 18B and mating screw threads (not illustrated) in female portion 18A may be employed. These various means of securement would be well known to the person ordinarily skilled in the art.

As a result, securing mechanism 18 is adapted for removably securing miniature medical implement member 20 and support sheath 10 to one another at their handle end 26 and proximal end 17, respectively, when miniature medical implement member 20 is advanced axially through support sheath 10 with working end 24 extending beyond distal end 15 of support sheath 10 to form a co-axial unit. Consequently, when miniature medical implement member 20 is secured to support sheath 10, support sheath 10 provides rigid support and prevents the very small diameter elongated portion 22 of miniature medical implement member 20 from breaking during an endoscopic medical procedure.

Besides working end 24 and handle end 26 employed with grasper 20 as described above (see FIG. 3), it will be understood that various other working ends and handle ends, as are known to the person of ordinary skill in the art, may be employed with miniature medical implements other than grasper 20, for use in the interlocking assembly of support sheath and miniature medical implement member of the invention. It is also noted that, as is well known to the person of ordinary skill in the art, various working ends may be bi-polar or mono-polar, and any particular working end may have variations in length, width, or style, such as a grasper working end may be of a claw style. In the discussion below with respect to FIGS. 6–15, various other representative miniature medical implement members are described which can be used in the interlocking assembly of the invention, but the description is not intended to limit the invention but only to provide a more complete description thereof.

Figure 6:
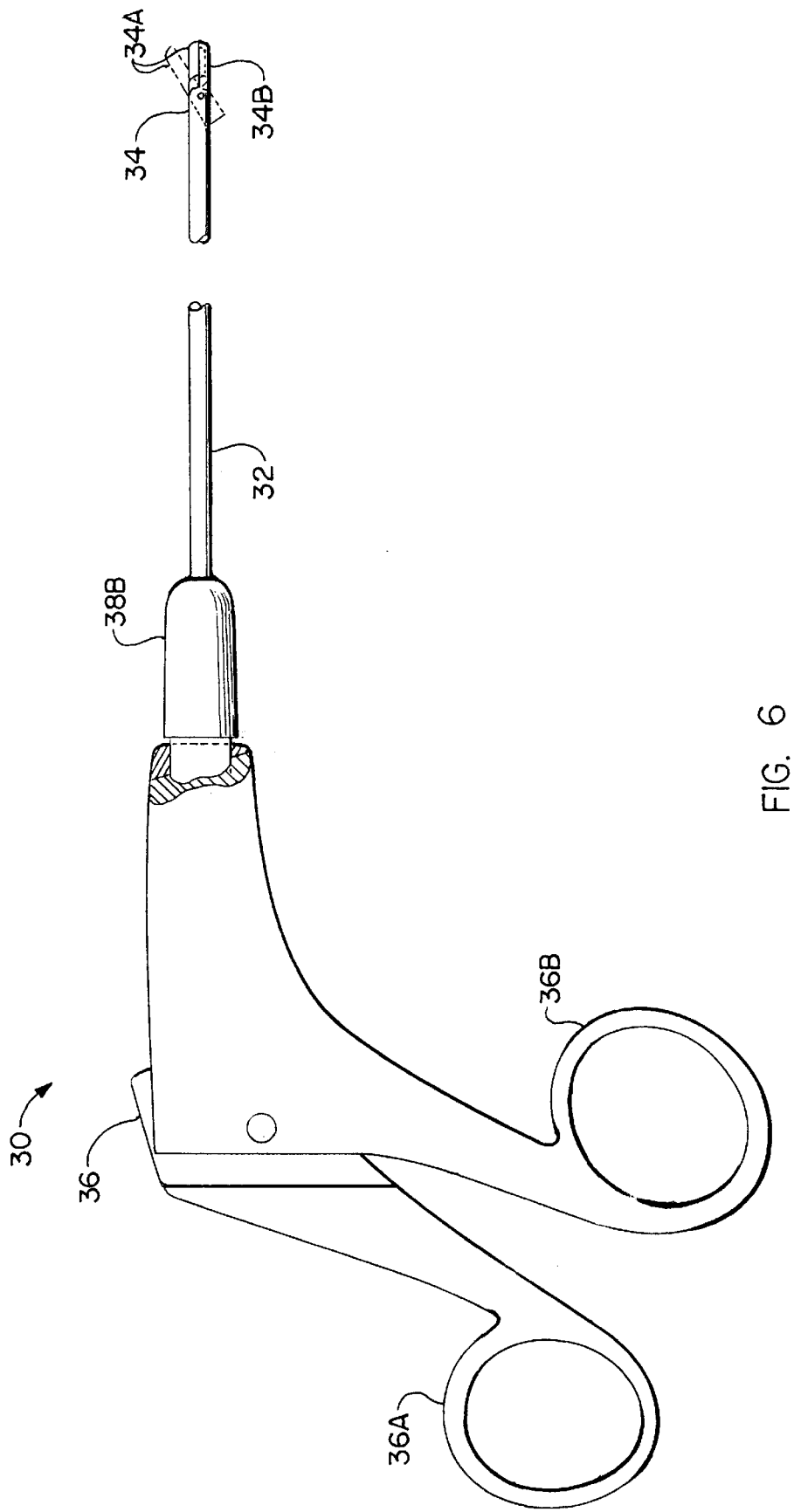
FIG. 6 is a side elevational view of a representative miniature medical implement portion, illustrated as a biopsy punch, of the present invention.

In FIG. 6, illustrated is biopsy punch 30 as a representative miniature medical implement member. Biopsy punch 30 is shown having elongated portion 32, working end 34, handle end 36, and male portion 38B. Working end 34 is suitably a cup mechanism having first cup arm 34A and second cup arm 34B. For ease of illustration, cup arms 34A, 34B are shown in the closed position, with first cup arm 34A again shown in broken lines to depict the open position. Cup arms 34A, 34B are connected in a manner known to the person of ordinary skill in the art, such as by a rod wire, (not illustrated), to handle end 36 in order to work cup arms 34A, 34B so that they can be employed to seize a tissue sample (not illustrated) to remove it for a biopsy. More particularly, handle end 36 is suitably illustrated as a scissors handle, having first scissors handle arm 36A and second scissors handle arm 36B that move relative to each other in a manner known to those ordinarily skilled in the art in order to work cup arms 34A, 34B of biopsy punch 30.

Figure 7:
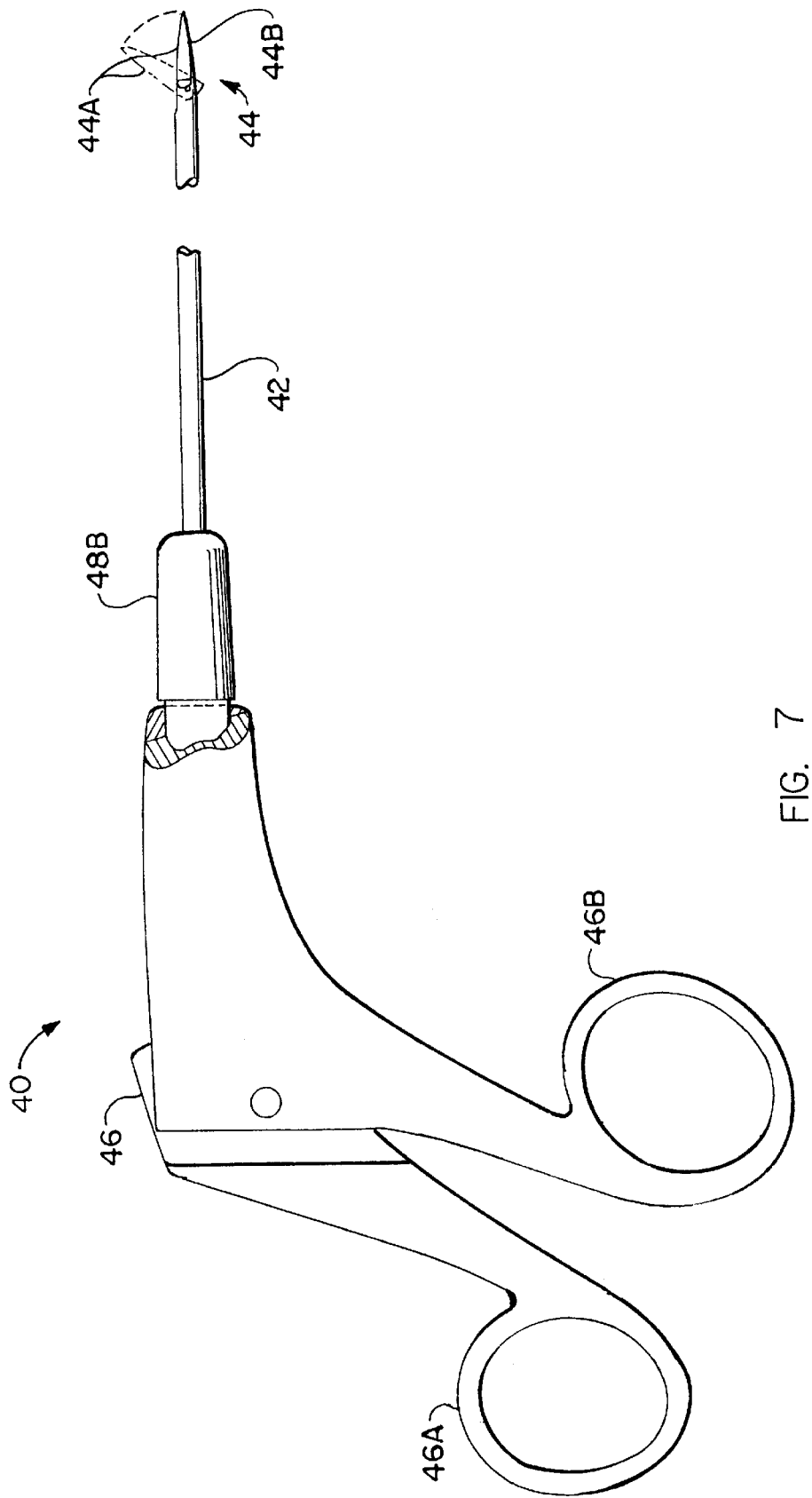
FIG. 7 is a side elevation view of a representative miniature medical implement portion, illustrated as a scissors, of the present invention.

Illustrated in FIG. 7 is scissors 40 as a representative miniature medical implement member. Scissors 40 has elongated portion 42, working end 44, and handle end 46. Working end 44 is suitably a scissors cutting mechanism having first scissors cutting arm 44A and second scissors cutting arm 44B. For ease of illustration, scissors cutting arms 44A, 44B are shown in the closed position, with first cutting arm 44A again shown in broken lines to depict the open position. Cutting arms 44A, 44B are connected in a manner known to the person of ordinary skill in the art, such as by a cable wire (not illustrated), to handle end 46 in order to work cutting arms 44A, 44B so that they may cut tissue (not illustrated) during surgery. More particularly, handle end 46 is suitably illustrated as a scissors handle, having first scissors handle arm 46A and second scissors handle arm 46B that move relative to each other in a manner known to those skilled in the art in order to work cutting arms 44A, 44B of scissors 40.

Illustrated in FIG. 8 is trocar 50 as a representative miniature medical implement member. Trocar 50 has elongated portion 52, working end 54, handle end 56, and male portion 58B. Working end 54 suitably terminates in cutting edge or cutting point 54' in order to cut tissue.

In FIG. 9, an irrigation-aspiration probe 60 is shown as a representative miniature medical implement member. Probe 60 is hollow since it is intended for irrigation-aspiration. Probe 60 has elongated portion 62, working end 64, handle end 66, and male portion 68B. Handle end 64 suitably is provided with two apertures 64A, 64B that are connected in a manner known to the person of ordinary skill in the art, such as by two respective lumens (not illustrated), to handle end 66 in order to provide passageway for irrigation and aspiration, respectively. More particularly, handle end 66 is suitably illustrated as a double trumpet valve having first trumpet valve 66A and second trumpet valve 66B. Valves 66A and 66B are fluidly connected to apertures 64A, 64B in a manner known to those skilled in the art in order to provide irrigation and aspiration, respectively, by way of apertures 64A, 64B of irrigation-aspiration needle probe 60. It is noted that use of one set of valve and aperture may be reversed with the other set of valve and aperture for interchanging which set of valve/aperture is used for irrigation and which set of valve/aperture is used for aspiration.

Illustrated in FIG. 10 is a electro-surgical scalpel 70 as a representative miniature medical implement member. Scalpel 70 has elongated portion 72, working end 74, handle end 76, and male portion 78B. Working end 74 suitably terminates in scalpel point 74'.

Illustrated in FIG. 11 is a scalpel 80 as a representative miniature medical implement member. Scalpel 80 has elongated portion 82, working end 84, handle end 86, and male portion 88B. Working end 84 suitably terminates in scalpel edge 84'.

Illustrated in FIG. 12 is scraper 90 as a representative miniature medical implement member. Scraper 90 has elongated portion 92, working end 94, handle end 96, and male portion 98B. Working end 94 suitably terminates in serrations 941.

Illustrated in FIG. 13 is manipulator 100 as a representative miniature medical implement member. Manipulator 100 has elongated portion 102, working end 104, handle end 106, and male portion 108B. Working end 104 suitably terminates in rounded tip 104'.

Illustrated in FIG. 14 is needle 110 as a representative miniature medical implement member. Electro-surgical needle 110 has elongated portion 112, working end 114, handle end 116, and male portion 118B. Working end 114 suitably terminates in needle tip 114'.

Illustrated in FIG. 15 is ball probe 120 as a representative miniature medical implement member. Ball probe 120 has elongated portion 122, working end 124, handle end 126, and male portion 128B. Working end 124 suitably terminates in ball tip 124'.

As noted previously, any of miniature medical implement members 20–120 shown in FIGS. 3 and 6–15 may be removably secured to miniature support sheath 10 to provide the innovative small diameter endoscopic surgical assembly of the invention and to practice the innovative endoscopic surgical procedure of the invention.

It will be understood that various details of the invention may be changed without departing from the scope of the invention. Furthermore, the foregoing description is for the purpose of illustration only, and not for the purpose of limitation—the invention being defined by the claims.

What is claimed is:

1. A surgical instrument assembly for performing an endoscopic medical procedure in a human or veterinary body, said assembly comprising:
   (a) a support sheath, having an elongated, tubular portion, a distal end, and a proximal end, and said support sheath being adapted for introduction into a tissue forming part of the body and for advancement therewithin;
   (b) a miniature medical implement member, having an elongated portion, a working end, and a handle end, and said miniature medical implement member being adapted for insertion into and advancement axially through said support sheath until the working end extends beyond the distal end of said support sheath; and
   (c) a securing mechanism adapted for securing said miniature medical implement member and said support sheath to one another at their handle end and proximal end, respectively, when said miniature medical implement member is advanced axially through said support sheath with the working end extending beyond the distal end of said support sheath to form a coaxial unit, said securing mechanism functioning to prevent movement of said miniature medical implement member with respect to said support sheath;
   whereby when said miniature medical implement member is secured to said support sheath, said support sheath provides rigid support and will prevent the elongated portion of the miniature medical implement member from breaking during an endoscopic medical procedure inside the body, and said miniature medical implement member and said support sheath form a unitary surgical instrument assembly which allows for a full range of movement during an endoscopic medical procedure without withdrawal of said medical implement member from said support sheath.

2. The surgical instrument assembly of claim 1, wherein the support sheath has a length between about 3.5 cm to 48.5 cm.

3. The surgical instrument assembly of claim 1, wherein the elongated portion of the support sheath has a cross-sectional outside diameter between about 2.1 mm to 2.2 mm and a cross-sectional inside diameter between about 1.85 mm to 1.95 mm.

4. The surgical instrument assembly of claim 1, wherein the miniature medical implement member has a length between about 5 cm to 50 cm.

5. The surgical instrument assembly of claim 1, wherein the elongated portion of the miniature medical implement member has a cross-sectional outside diameter between about 1.73 mm to 1.84 mm.

6. The surgical instrument assembly of claim 1, wherein the miniature medical implement member is selected from the group consisting of a trocar, a scalpel, a scraper, a ball probe, an irrigation-aspiration probe, a manipulator, a needle, a forceps, a scissors, and a biopsy punch.

7. A surgical instrument assembly for performing an endoscopic medical procedure in a human or veterinary body, said assembly comprising:

(a) a support sheath, having an elongated, tubular portion, a distal end, and a proximal end, and said support sheath being adapted for introduction into a tissue forming part of the body and for advancement therewithin, and wherein the elongated portion of the support sheath has a cross-sectional outside diameter between about 2.1 mm to 2.2 mm and a cross-sectional inside diameter between about 1.85 mm to 1.95 mm;

(b) a miniature medical implement member, having an elongated portion, a working end, and a handle end, and said miniature medical implement member being adapted for insertion into and advancement axially through said support sheath until the working end extends beyond the distal end of said support sheath, and the elongated portion having a cross-section outside diameter between 1.73 mm to about 1.84 mm; and (c) a securing mechanism adapted for securing said miniature medical implement member and said support sheath with one another at their handle end and proximal end, respectively, when said miniature medical implement member is advanced axially through said support sheath with the working end extending beyond the distal end of said support sheath to form a coaxial unit, said securing mechanism functioning to prevent movement of said miniature medical implement member with respect to said support sheath;

whereby when said miniature medical implement member is secured to said support sheath, said support sheath provides rigid support and will prevent the elongated portion of the miniature medical implement member from breaking during an endoscopic medical procedure inside the body, and said miniature medical implement member and said support sheath form a unitary surgical instrument assembly which allows for a full range of movement during an endoscopic medical procedure without withdrawal of said medical implement member from said support sheath.

8. The surgical instrument assembly of claim 7, wherein the support sheath has a length between about 3.5 cm to 48.5 cm.

9. The surgical instrument assembly of claim 7, wherein the miniature medical implement member has a length between about 5 cm to 50 cm.

10. The surgical instrument assembly of claim 7, wherein the miniature medical implement member is selected from the group consisting of a trocar, a scalpel, a scraper, a ball probe, an irrigation-aspiration probe, a manipulator, a needle, a forceps, a scissors, and a biopsy punch.

11. A medical process for performing an endoscopic medical procedure in a target area within a human or veterinary body comprising:

(a) providing a support sheath comprising and elongated, tubular portion, a distal end, and a proximal end, and advancing said support sheath through a puncture wound in the body with the proximal end outside of the body and the distal end inside of the body, whereby access within the body is gained and said support sheath is in position in the target area;

(b) inserting into said support sheath a miniature medical implement member comprising an elongated portion, a working end, and a handle end, and advancing said miniature medical implement member axially through said support sheath until the working end extends beyond the distal end of said support sheath;

(c) securing said miniature medical implement member and said support sheath to one another at their handle end and proximal end, respectively, when said miniature medical implement member is advanced axially through said support sheath with the working end extending beyond the distal end of said support sheath so as to form a co-axial unit, said securing mechanism preventing movement of said miniature medical implement member with respect to said support sheath; and (d) performing the endoscopic medical procedure using the co-axial unit within the body;

whereby said support sheath provides rigid support for said miniature medical implement member such that said miniature medical implement member is prevented from breaking along the length of its elongated portion during the endoscopic medical procedure, and said miniature medical implement member and said support sheath form a unitary surgical instrument assembly which allows for a full range of movement during an endoscopic medical procedure without withdrawal of said medical implement member from said support sheath.

12. The medical process of claim 11, including between steps (a) and (b) inserting and fixedly securing a trocar within said support sheath to facilitate entering the body.

13. The medical process of claim 11, wherein the support sheath has a length from about 3.5 cm to 48.5 cm.

14. The medical process of claim 11, wherein the elongated portion of the support sheath has a cross-sectional outside diameter of about 2.1 mm to 2.2 mm and a cross-sectional inside diameter of about 1.85 mm to 1.95 mm.

15. The medical process of claim 11, wherein the miniature medical implement member has a length between about 5 cm to 50 cm.

16. The medical process of claim 11, wherein the elongated portion of the miniature medical implement member has a cross-sectional outside diameter between about 1.73 mm to 1.84 mm.

17. The medical process of claim 11, wherein the miniature medical implement member is selected from the group consisting of a trocar, a scalpel, a scraper, a ball probe, an irrigation-aspiration probe, a manipulator, a needle, a forceps, a scissors, and a biopsy punch.

* * * * *